US00PP11218P

United States Patent [19]

Rackley

[11] Patent Number: Plant 11,218

[45] Date of Patent: Feb. 15, 2000

[54] PITTOSPORUM PLANT NAMED 'WILLEII'

[76] Inventor: Jon G. Rackley, 417 Lake North Rd., Eustis, Fla. 32726

[21] Appl. No.: 09/004,261

[22] Filed: Jan. 8, 1998

[51] Int. Cl.[7] ..... A01H 5/00

[52] U.S. Cl. ..... Plt./234

[58] Field of Search ..... Plt./234

[56] References Cited

U.S. PATENT DOCUMENTS

| | | | |
|---|---|---|---|
| P.P. 4,919 | 11/1982 | Turner | Plt./234 |
| P.P. 5,233 | 5/1984 | Turner | Plt./234 |
| P.P. 5,893 | 3/1987 | Rackley | Plt./234 |

*Primary Examiner*—Howard J. Locker
*Assistant Examiner*—Kent L. Bell
*Attorney, Agent, or Firm*—James A. Lucas; Driggs, Lucas, Brubaker & Hogg Co., L.P.A.

[57] ABSTRACT

A new and distinct variety of Pittosporum characterized by its growth habit and distinctive leaf variegation with the adaxial side of the leaf blades having a spotted and blotched basic field with a moderately narrow and discontinuous border that is mainly located along the margins of the distal half of the leaf blade and the abaxial side of the leaf blade having a basic field with a notable absence of the spots and blotches found on the adaxial side, but which nevertheless, has a border that is a reverse replica of that at the adaxial side. The leaf margin has an undulated and pronounced recurved form.

2 Drawing Sheets

BACKGROUND OF THE DISCLOSURE

The invention relates generally to a new and distinct plant variety of the Pittosporaceae family which has been named *Pittosporum tobira* 'Willeii'.

*P. tobira*, also known as a Japanese Pittosporum, is a hardy and serviceable hedge plant originally from China or Japan. It has thick rubbery evergreen leaves and creamy-white flowers which are borne in small terminal clusters during May. Although the flowers are not usually very conspicuous, they have a pronounced fragrance.

Certain plant varieties of *P. tobira* are well known. Among these are the 'Wheelerii' variety (unpatented) and its variegated sport 'Lauralee' (U.S. Plant Pat. No. 5,893), the 'Variegatum' variety (unpatented), the 'Compacta Glen Special' (unpatented) variety, and a variety commonly called 'Green Pittosporum'. The 'Green Pittosporum' (unpatented) is believed to be the same variety also known as Mock-Orange or Australian Laurel.

The 'Wheelerii' and 'Lauralee' varieties are the most compact varieties, while the 'Compacta Glen Special' and the 'Variegatum' are moderate sized Pittosporums. The 'Green Pittosporum' is also a larger plant than the above mentioned dwarf and compacta varieties and is known to grow to a height of 15–20 feet.

In addition to the varieties mentioned, above, there have been two varieties of *P. tobira* patented by Turner: the 'Turner's Dwarf Tricolor' (U.S. Plant Pat. No. 5,233) and 'Turner's Variegated Dwarf' (U.S. Plant Pat. No. 4,919) marketed as 'Turner's Dwarf Bicolor'.

SUMMARY OF THE INVENTION

I discovered this new variety of Pittosporum as a naturally occurring sport or bud variation of a specimen of the 'Compacta Glen Special' variety which was being grown in a nursery near Eustis, Fla. I have caused the plant to be reproduced asexually by propagation of stem cuttings at the nursery through successive propagation and find that it comes true in successive generations. It has been ascertained that this new variety has certain stable and reproducible characteristics which distinguish it from its antecedents and known related varieties. This new variety of Pittosporum was asexually reproduced by the following method:

Semi hardwood, terminal cuttings are taken 4–5 inches long. Leaves are taken off the lower ½ of stems and placed approximately 1½ inches deep in a rooting media of ½ Canadian peatmoss, ½ horticultural perlite. Cuttings are then placed in open air mist beds where intermittent mist is applied for approximately 8 weeks. Cuttings are then hardened off for another 8 weeks before planting into containers.

This new plant is distinguishable from *P. tobira* 'Compacta Glenn Special' in that the leaf blades of the 'Compacta Glen Special' are not variegated and have a solid green field that lacks the spotted and blotched basic field and the border color characteristics of this new variety. The 'Compacta Glen Special' variety has a slightly faster growth rate and thus at comparable ages, especially during the first year of growth, produces specimens that are slightly larger than the new variety. Terminal stem lengths on similar aged container grown plants and grown with similar environments and fertility average 12 mm longer on the 'Compacta Glen Special' variety than on the new variety.

The new variety is distinguishable from the 'Wheelerii' variety in that the leaf blades of 'Wheelerii' are not variegated and have a solid green field that lacks both the spotted and blotched and basic field and the border color characteristics of the new variety. Terminal stem lengths average 31 mm longer on the new variety when compared to terminal stem lengths of similarly grown 'Wheelerii' specimens. Leaves differ also in their margins with those of the new variety having undulated and prominently recurved leaf margins while those of the 'Wheelerii' variety have neither undulation nor recurved margins.

The variegated variety of *P. tobira* 'Wheelerii' known as 'Lauralee' (U.S. Plant Pat. No. 5,893), although similar to the new variety in its unique variegated color pattern including spots and blotches is distinguishable from the new variety in several ways. First the plant habits differ in that the 'Lauralee' variety maintains a lower profile seldom attaining more than 3 feet in height, naturally forming a dense mound. In contrast to this, the new variety has attained a height of almost 6 feet after being planted in the Florida landscape for two (2) years, and has a similar if not identical habit to its green parent 'Compacta Glen Special'. The new variety is more openly branched than the 'Lauralee' variety which is reflected in the average terminal stem length being approximately 40 mm longer than the 'Lauralee' variety stem length. Leaf margins are also a distinguishing characteristic with the new variety having an undulated and pronounced recurved form. The leaf margins found on the 'Lauralee' variety are similar to its all green parent, 'Wheelerii', and are not undulated and lack the recurve character found on the new variety.

The new variety is distinguishable from the 'Variegatum' variety in that spots and blotches are readily apparent on fully expanded upper adaxial leaf surfaces of the new variety whereas they are absent on 'Variegatum' leaf surfaces. The lack of spots and blotches on both Turner's varieties described in U.S. Plant Pat. No. 's 5,233 and 4,919 clearly distinguish these from the new variety.

The general objective of the invention has been to develop a compact variety of *P. tobira* which would: maintain a compact growth habit; be stable in its variegated leaf color and be consistently reproducible by means of asexual reproduction; maintain a higher degree of disease resistance to alternaria foliar leaf spots than the 'Wheelerii' variety and its variegated form, especially 'Lauralee' variety U.S. Plant Pat. No. 5,893; and be clearly distinguishable from all other varieties of *P. tobira* known to the inventor.

Thus through successive propagation, it has been ascertained that specimens of the new plant variety generally resemble specimens of the 'Compacta Glen Special' variety but are distinguishable therefrom and from other related varieties known to the inventor by a growth habit which is evident in specimens propagated and grown near Eustis, Fla. under the conditions set forth hereinafter as combining the following principal characteristics:

1) Growth habit, compactness, branch structure, leaf size, structure and form comparable to 'Compact Glen Special' variety, but have a slightly slower growth rate that results in specimens which, during the first year of growth, are evidently slightly smaller in size than specimens of the 'Compacta Glen Special' variety of comparable age and furthermore are distinct and characteristically variegated as follows:

a. on the adaxial side — spotted and blotched basic field with a moderately narrow and discontinuous border that is mainly located along the margins of the distal half of the leaf blade and
b. on the abaxial side — a basic field with a notable absence of the spots and blotches found on the adaxial side, but which nevertheless, has a border that is a reverse replica of that at the adaxial side.

2) The leaf blades on the adaxial side have a glossy and shiny surface with a. a basic field that in color is dominated by strong to moderate yellow-green for new expanding leaves, by moderate yellow-green for newly expanded leaves, and by grayish yellow-green for older leaves;
b. spots and blotches that are generally darker than the basic field side and in color are dominated by olive-green on newly expanded and older leaves; and
c. a border that is generally lighter than the basic field and in color is dominated by brilliant yellow-green new expanding leaves, and by moderate and light yellow-green for newly expanded and older leaves.

3) The leaf blades on the abaxial side have a slightly duller appearance and lack the glossy sheen as found on the adaxial leaf surface with a. a basic field that in color is dominated by moderate yellow-green on new and older leaves alike; and
b. a border that is generally lighter than the basic field and in color is dominated by bright to strong yellow-green on new expanding leaves and by light yellow-green on newly expanded and older leaves.

DESCRIPTION OF THE DRAWINGS

This new variety of Pittosporum plant is illustrated by the accompanying photographic drawings, depicting the plant by the best possible color representation using color photography.

BOTANICAL DESCRIPTION OF THE PLANT

Figure 1:
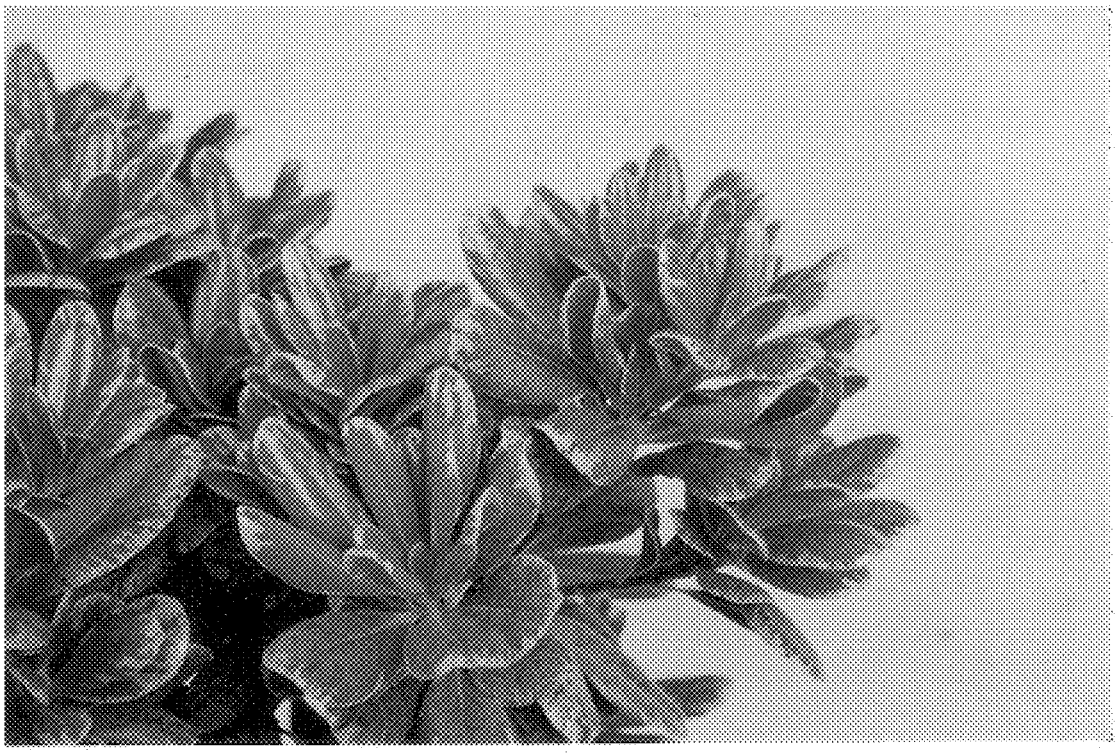
FIG. 1: Shows a side elevation of 18 month old plant in a 9½ in. diameter container.
Figure 2:
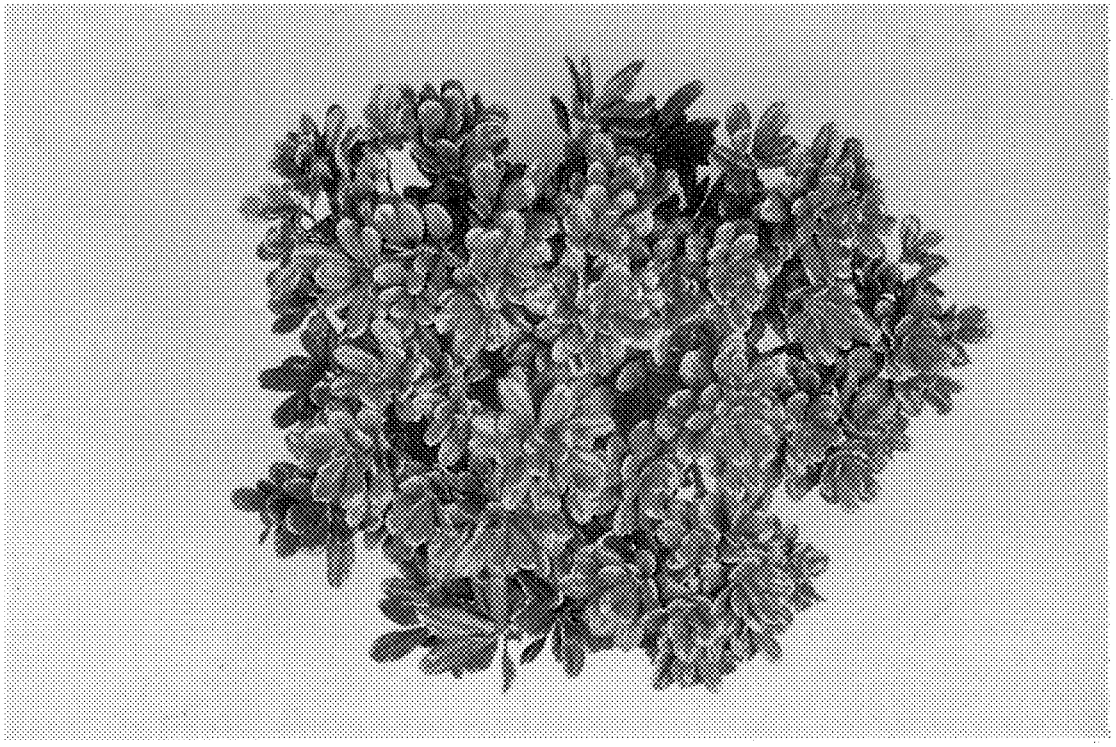
FIG. 2: Shows a top view of the plant shown in FIG. 1.
Figure 3:
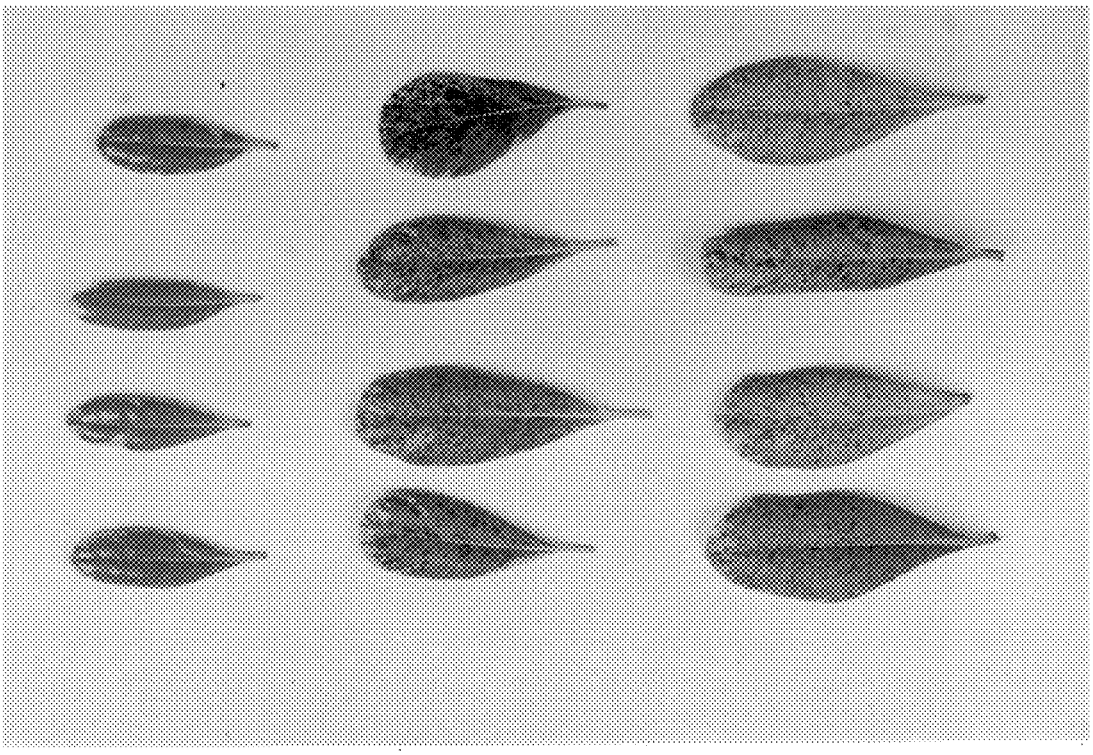
FIG. 3: Shows the adaxial side of leaf blades of the plant at three stages of maturity.
Figure 4:
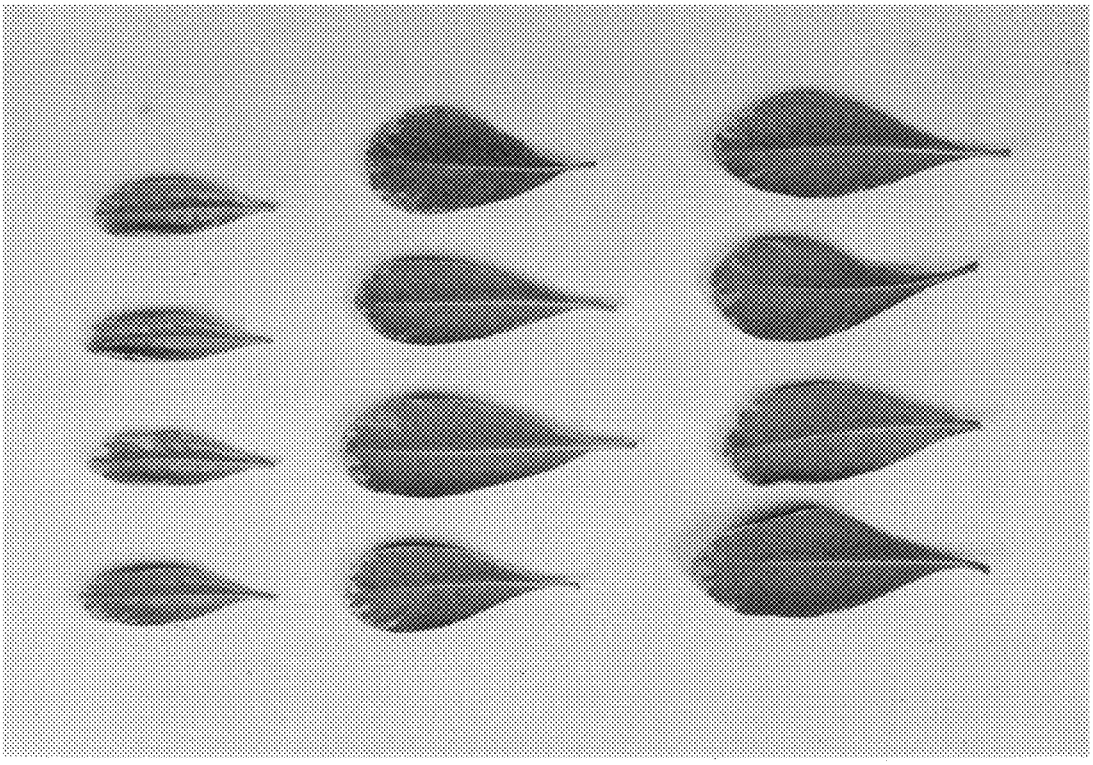
FIG. 4. Shows the abaxial side of leaf blades of the plant at three stages of maturity.

Color values presented in this disclosure were taken from the Munsell Color Cascade. Color definitions of ordinary meaning are presented where appropriate and properly descriptive. Colors are approximate as color depends on horticultural practices such as light level and fertilization rate, among others, without, however any variance in genotype.

In order to point out more specifically the most notable aspects and novel characteristics of the plant of this invention as set forth above, the following detailed botanical description presents the general as well as the characteristics of *P. tobira* 'Willeii'.

Parentage: Naturally occurring sport of *P. tobira* 'Compacta Glen Special'.

Foliage:

*Type.*—Simple, stalked and abundant.

*Arrangement.*—Alternate.

*Shape.*—Obovate, blunt or rounded at apex, tapering to a short petiole.

*Size.*—50–90 mm long, 13–30 mm wide.

*Margin.*—Smooth, entire, recurved — most prominent in mid and distal portions.

*Texture.*—Course, leathery, and glabrous.

*Surface.*—Adaxial — smooth and glossy. abaxial — smooth and lacks glossiness.

*Veins.*—Pinnate, not prominate except at petiole junction, slightly more pronounced on undersides.

*Petiole.*—5.5 mm–12 mm in length, average 9.5 mm.

Color:

*New leaves* (*Less than* 1 *month old*).—Adaxial surface — Basic field — 5GY5/8, 7.5GY5/6, 117–120 Strong to moderate yellow green. Marginal variegation— 2.5GY8/8, 116 brilliant yellow green. Spots and blotches — None. Abaxial surface — Basic field — 5GY5/6, 120 moderate yellow green. 7.5GY5/6, 120 moderate yellow green. Marginal variegation — 2.5GY8/8, 116 brilliant yellow green to 10Y8/8, 98–99 strong greenish yellow. Spots and blotches — None. Petiole and primary portion of mid rib — 10GY8/6, 135 light yellow green. 2.5GY8/4, 119 light yellow green. 5GY8/4, 119 light yellow green.

*Mid aged leaves* (1–6 *months old*)—Adaxial surface — Basic field — 7.5GY5/4, 120 moderate yellow green. 5GY5/4, 120 moderate yellow green. Marginal variegation — 5GY7/4, 120 moderate yellow green. 2.5GY8/6, 119 light yellow green. Spots and blotches — 5GY4/4, 125 moderate olive green. 7.5GY4/4, 125 moderate olove green. Abaxial surface — Basic field — 7.5GY5/4, 120 moderate yellow green. 5GY5/4, 120 moderate yellow green. Marginal variegation — 2.5GY8/6, 119 light yellow green. Spots and blotches — None. Petiole and primary portion of midrib — 5GY7/4, 120 moderate yellow green. 2.5GY7/4, 120 moderate yellow green.

*Old leaves* (*over* 6 *months old*).—Adaxial surface — Basic field — 5GY7/2, 122 grayish yellow green. 2.5GY7/2, 122 grayish yellow green. 7GY7/2, 122 grayish yellow green. Marginal variegation — 2.5GY8/4, 119 light yellow green. 5GY8/4, 119 light yellow green. Spots and blotches — 5GY4/4, 125 moderate olive green. 7.5GY4/4, 125 moderate olive green. Abaxial surface — Basic field — 5GY5/4, 120 moderate yellow green. 7.5GY5/4, 120 moderate yellow green. Marginal variegation — 5GY8/4, 119 light yellow green. 2.5GY8.5/6, 119 light yellow green. Spots and blotches — None. Petiole and primary portion of midrib — 5GY8/4, 119 light yellow green. 2.5GY/4, 120 moderate yellow green.

Flowers: The characteristics of the flower have not been systematically observed for reasons of the absence thereof on specimens grown to date.

Disease resistance: 'Willeii' does not require the application of a fungicide to control alternaria foliar leaf spots.

I claim:

1. A new and distinct variety of Pittosporum plant as described and illustrated, characterized particularly as to novelty by its growth habit and distinctive leaf variegation with a basic field of spots and blotches on the adaxial leaf surface along with a moderately narrow, discontinuous border on both the adaxial and abaxial leaf surfaces and a margin having an undulated and pronounced recurved form.

* * * * *